United States Patent [19]
Ellis

[11] Patent Number: 5,938,632
[45] Date of Patent: Aug. 17, 1999

[54] RADIOFREQUENCY TRANSMYOCARDIAL REVASCULARIZATION APPARATUS AND METHOD

[75] Inventor: Louis Ellis, St. Anthony, Minn.

[73] Assignee: SciMed Life Systems, Inc., Maple Grove, Minn.

[21] Appl. No.: 08/810,830

[22] Filed: Mar. 6, 1997

[51] Int. Cl.[6] .................................................. A61N 1/30
[52] U.S. Cl. ............................................................... 604/19
[58] Field of Search ........................ 604/22; 606/13–16, 606/39, 40, 45–47

[56] References Cited

U.S. PATENT DOCUMENTS

| | | | |
|---|---|---|---|
| 4,790,311 | 12/1988 | Ruiz | 128/303.1 |
| 4,896,671 | 1/1990 | Cunningham et al. | 128/642 |
| 5,047,026 | 9/1991 | Rydell | 606/48 |
| 5,093,877 | 3/1992 | Aita et al. | 385/34 |
| 5,358,485 | 10/1994 | Vance et al. | 604/22 |
| 5,364,393 | 11/1994 | Auth et al. | 606/34 |
| 5,370,675 | 12/1994 | Edwards et al. | 607/101 |
| 5,380,316 | 1/1995 | Aita et al. | 606/7 |
| 5,389,096 | 2/1995 | Aita et al. | 606/15 |
| 5,403,311 | 4/1995 | Abele et al. | 606/49 |
| 5,423,846 | 6/1995 | Fischell | 606/180 |
| 5,522,815 | 6/1996 | Durgin, Jr. et al. | 606/50 |
| 5,586,982 | 12/1996 | Abela | 606/28 |
| 5,591,159 | 1/1997 | Taheri | 606/15 |
| 5,593,405 | 1/1997 | Osypka | 606/15 |
| 5,607,405 | 3/1997 | Decker et al. | 604/264 |
| 5,620,414 | 4/1997 | Campbell, Jr. | 604/22 |
| 5,672,174 | 9/1997 | Gough et al. | 606/41 |
| 5,681,308 | 10/1997 | Edwards et al. | 606/41 |
| 5,683,366 | 11/1997 | Eggers et al. | 604/114 |
| 5,697,882 | 12/1997 | Eggers et al. | 604/114 |
| 5,700,259 | 12/1997 | Negus et al. | 606/14 |
| 5,703,985 | 12/1997 | Owyang | 606/13 |
| 5,713,894 | 2/1998 | Murphy-Chutorian et al. | 606/15 |
| 5,725,521 | 3/1998 | Mueller | 606/7 |
| 5,725,523 | 3/1998 | Mueller | 606/15 |

FOREIGN PATENT DOCUMENTS

| | | |
|---|---|---|
| 296 09 350 U1 | 10/1996 | Germany. |
| 195 37 084 A1 | 4/1997 | Germany. |
| WO 96/35469 | 11/1996 | WIPO. |
| WO 96/39963 | 12/1996 | WIPO. |
| WO 97/18768 | 5/1997 | WIPO. |
| WO 97/29803 | 8/1997 | WIPO. |
| WO 97/32551 | 9/1997 | WIPO. |
| WO 97/44071 | 11/1997 | WIPO. |

OTHER PUBLICATIONS

Abstract entitled "Transventricular Revascularization by Laser", *Lasers in Surgery and Medicine*, 1982, 1 page.

Abstract entitled "Analysis of Photoproducts, Free Radicals and Particulate Debris Generated During In–Vivo Argon Laser Myoplasty", *Lasers in Surgery and Medicine*, 1991, 1 page.

Isner, J., "Right Ventricular Myocaridal Infarction", *The Journal of the American Medical Association*, V259, N5, Feb. 5, 1988, 12 pages.

Abstract entitled "Proliferative Activity in Peripheral and Coronary Atherosclerotic Plaque . . . ", *J. Clin. Invest.*, Apr., 1993, 1 page.

A. Vineberg et al., "Creation of Intramyocardial Pathways to Channel Oxygenated Blood Between Ventricular Arteriolar Zones", *Canad. Med. Assoc. Journal*, Feb. 4, 1967, vol. 96, pp. 277–279.

(List continued on next page.)

*Primary Examiner*—John D. Yasko
*Assistant Examiner*—Manuel Mendez
*Attorney, Agent, or Firm*—Crompton, Seager & Tufte, LLC

[57] ABSTRACT

An RF TMR catheter having an elongate shaft and a metallic cutting tip disposed at the distal end of the shaft. A hood is disposed proximate the distal end of the shaft for limiting the depth of penetration of the metallic cutting tip.

5 Claims, 3 Drawing Sheets

OTHER PUBLICATIONS

A. Vineberg, M.D., "Results of 14 years' Experience in the Surgical Treatment of Human Coronary Artery Insufficiency", *Canad. Med. Assoc. Journal*, Feb. 13, 1965, vol. 92, pp. 325–332.

A. Vineberg et al., "The Ivalon Sponge Procedure for Myocardial Revascularization", *Surgery*, vol. 47, No. 2, Feb., 1960, pp. 268–289.

A. Vineberg et al., "Investigative Surgery: Treatment of Acute Myocardial Infarction by Endocaridal Resection", *Surgery*, vol. 57, No. 6, Jun., 1965, pp. 832–835.

P. Walter et al., "Treatment of Acute Myocardial Infarction by Transmural Blood Supply From the Ventricular Cavity", *Europ. Surg. Res.*, 3:130–138 (1971).

H.A. Khazei et al., "Myocardial Canalization: New Method of Myocardial Revascularization", *The Annals of Thoracic Surgery*, vol. 6, No. 2, Aug., 1968, pp. 163–171.

J. Hershey et al., "Transmyocardial Puncture Revascularization: a Possible Emergency Adjunct to Arterial Implant Surgery", *Geriatrics*, Mar., 1969, pp. 101–108.

Press Release dated Oct. 21, 1996, entitled "Doctors Demonstrate Proof of Blood Flow Through Open TMR Channels Created with PLC Systems . . . ", PLC Systems, Inc., 1 page.

Press Release dated Oct. 10, 1996, entitled "Texas Fieart Institute Presents Study Comparing the Use of CO2, Holmrum and Excimer Lasers for TMR", 1 page.

M. L. Goldman et al., "Nonoperative Portacaval Shunt in Swine," *Investigative Radiology*, vol. 25, No. 5, May 1990, pp. 574–578.

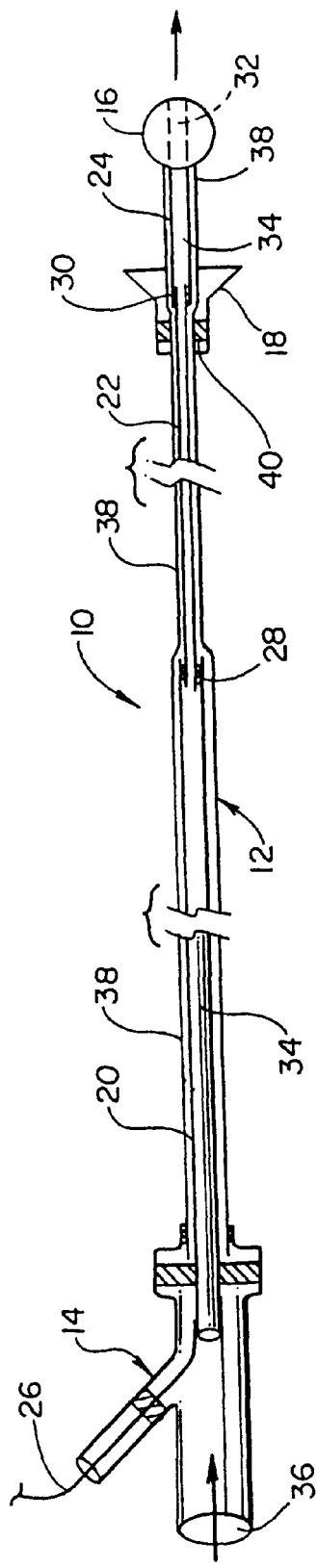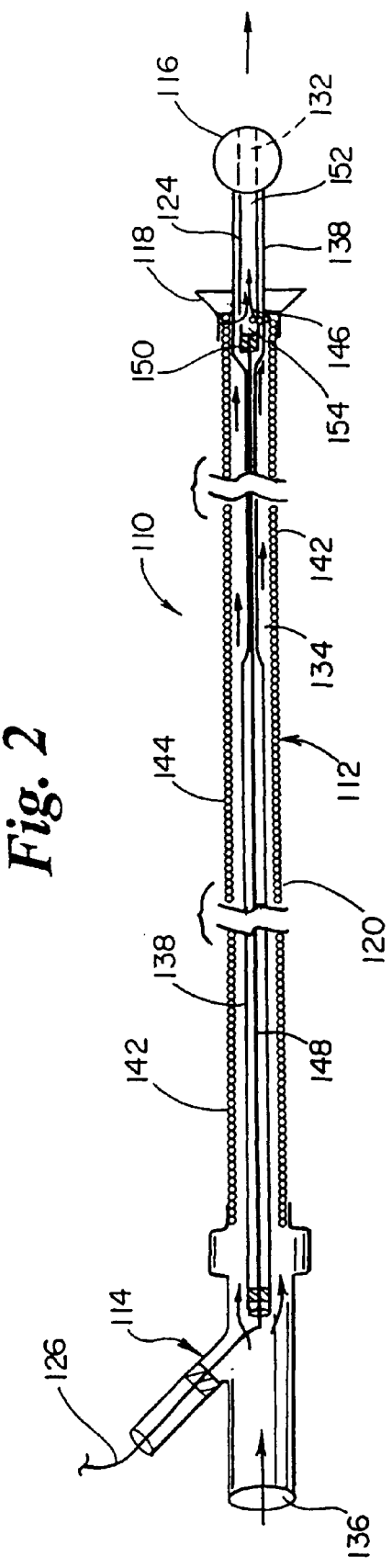

RADIOFREQUENCY TRANSMYOCARDIAL REVASCULARIZATION APPARATUS AND METHOD

FIELD OF THE INVENTION

The present invention pertains to a device and method for performing transmyocardial revascularization (TMR) using radiofrequency (RF) energy.

BACKGROUND OF THE INVENTION

A number of techniques are available for treating cardiovascular disease such as cardiovascular by-pass surgery, coronary angioplasty, laser angioplasty and atherectomy. These techniques are generally applied to by-pass or open lesions in coronary vessels to restore or increase blood flow to the heart muscle. In some patients, the number of lesions is so great, or the location so remote in the patient's vasculature, that restoring adequate blood flow to the heart muscle is difficult.

TMR has been developed as an alternative to these techniques which are directed at by-passing or removing lesions. TMR is preformed by boring channels directly into the myocardium of the heart. It has been found that creating several channels may be useful.

In one procedure, laser catheters are advanced into the left ventricle. Laser radiation is then focused on the myocardium to create a channel. Channels cut by a laser have a width proportionate to the width of the focused laser radiation used to make the channels.

TMR is also performed by cutting a channel with a sharpened probe or blade. When this procedure is performed with a blade, tissue is generally merely pierced or cut.

Lasers used to perform TMR can be costly and the depth of the channels formed can be difficult to control. Similarly, controlling the depth of the channels formed by a blade has been difficult to control.

SUMMARY OF THE INVENTION

The present invention pertains to an apparatus and method for performing TMR using RF energy. The apparatus and method of the present invention provides a means for performing TMR by creating channels in the myocardium of the patient's heart which can vary in depth and width. The depth of the channels are generally believed to be directly proportional to the distance which the catheter of the present invention is advanced into the patient's myocardium. The width of channels are similarly believed to be proportional to the width of the cutting tip. Various apparatus are provided for controlling or limiting the penetration into the myocardium.

In one embodiment, an RF TMR catheter is provided having an elongate metallic shaft having a proximal end and a distal end. A lumen is defined through the elongate shaft. An insulating sheath surrounds the shaft and a metallic cutting tip is disposed at the distal end of the shaft. The cutting tip has a lumen defined therethrough in fluid communication with the shaft lumen.

A stop transversely extends from the shaft proximate and proximal the tip. The stop can include a generally conical hood. The tip can be generally spherically shaped. The tip can also comprise a radiopaque material.

The shaft can include a hypotube. The hypotube can comprise stainless steel and/or a superelastic alloy such as Nitinol. The insulating sheath can include polytetrafluoroethylene (PTFE) or polyethylene (PE).

An alternate embodiment of a TMR catheter in accordance with the present invention, includes an elongate shaft having a proximal end and a distal end and a lumen defined therethrough. A coil member, at least in part, defines the shaft lumen. A sheath is disposed around the coil. A cutting tip is disposed proximate the distal end of the shaft. The cutting tip can define a lumen therethrough in fluid communication with the shaft lumen.

The coil preferably includes adjacent windings. The sheath surrounding the coil can comprise a heat shrink polymer. The catheter also includes a core wire extending from the proximal end of the shaft to the cutting tip. The core wire is covered with polymer insulating sheath.

Yet another embodiment of a TMR catheter is provided having an elongate outer shaft having a proximal end and a distal end and a lumen defined therethrough. The distal end of the shaft defines a distally disposed orifice. An elongate inner shaft has a proximal end and a distal end. The inner shaft extends substantially through the shaft lumen. The cutting tip is disposed at the distal end of the inner shaft.

The inner shaft is longitudinally shiftable within the outer shaft such that the cutting tip can be moved from a first position proximate the distal end of the outer shaft to a second position distal of the first position. Stop means is provided for limiting the distance of the second position from the first position. The distal end of the outer shaft can define a hood which contains the tip in the first position. The distal end of the shaft can be atraumatic and/or radiopaque.

The catheter can include a centering means for generally transversely centering the distal end of the shaft relative to the orifice. The centering means can define apertures in fluid communication with the shaft lumen and the orifice.

In yet another embodiment of a TMR catheter in accordance with the present invention, an elongate outer shaft having a proximal end and a distal end, and a lumen defined therethrough is provided. An elongate inner shaft having a proximal end and a distal end extends through at least a portion of the shaft lumen to proximate the distal end of the outer shaft. The cutting tip is disposed at the distal end of the inner shaft. A hood is disposed at the distal end of the outer shaft. The hood is moveable between a first position proximate the tip and a second position proximal of the first position.

The distal tip is preferably disposed within the hood in the first position, the hood can have an atraumatic distal end which can be radiopaque. The hood can include a pleated, accordion-like, collapsible section which at least partially collapses as the hood moves from the first position to the second position. The hood will return to its original position after collapsing forces are removed. The accordion acts as a spring.

BRIEF DESCRIPTION OF THE DRAWINGS

FIG. 1 is a cross sectional view of an RF TMR catheter in accordance with the present invention;

FIG. 2 is a cross sectional view of an alternate embodiment of an RF TMR catheter in accordance with the present invention;

DETAILED DESCRIPTION OF THE INVENTION

Figure 3:
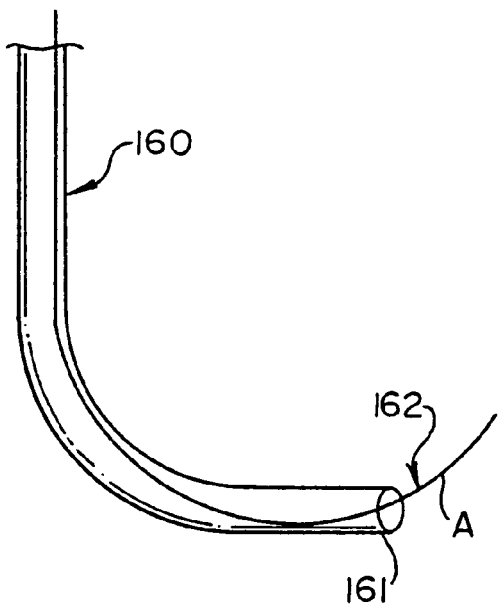
FIG. 3 is a schematic view of a generic non-coil shaft catheter advanced through a guide catheter.

Referring now to the drawings wherein like reference numerals refer to like elements throughout the several views, a radiofrequency transmyocardial revascularization (RF TMR) catheter 10 is shown in accordance with the present invention. Catheter 10 includes an elongate shaft 12 having a proximal end and a distal end. The proximal end of shaft 12 is connected to manifold 14. The distal end of shaft 12 is connected to an RF cutting tip 16. Proximate the distal end of shaft 12, and proximal of cutting tip 16 is a tip advancement limiting hood 18.

Shaft 12 can include a relatively rigid first shaft section 20 which extends for approximately 80 percent to 90 percent of the length of the shaft. The first shaft section 20 can be made from, for example, a stainless steel hypotube. Shaft 12 preferably includes a more flexible intermediate shaft section 22. Shaft section 22 is preferably more flexible than shaft section 20 to enhance steerability of catheter 10. Intermediate shaft section 22 can be formed from, for example, a superelastic alloy tube such as a Nitinol hypotube. A short distal shaft section 24, relatively more rigid than section 22, can interconnect intermediate shaft section 22 with tip 16. Section 24 can be formed from a stainless steel hypotube.

Shaft section 20 is preferably connected to a source of RF energy by a lead wire 26. A conductive path for RF energy is then formed through shaft section 20, a spot weld bond 28 between shaft section 20 and shaft section 22, a spot weld or conductive bond 30 between shaft sections 22 and 24 and a conductive bond between shaft 24 and tip 16.

Tip 16 is preferably spherical in shape and has a lumen 32 defined therethrough. Shaft sections 20, 22 and 24 define a lumen 34 in fluid communication with lumen 32. This arrangement allows fluid such as drugs or dyes to be introduced through a port 36, as shown by the arrow, into lumen 34 to be discharged distally through lumen 32 as shown by the arrow adjacent tip 16. By applying a suction at port 36, tissue and fluid can be aspirated in the opposite direction.

Shaft sections 20, 22 and 24 are preferably insulated by an exterior sheath 38. Sheath 38 is intended to shield the patient from RF energy traveling through shaft 12 to tip 16. Sheath 38 can be formed from various biocompatiable materials known to those skilled in the art of catheter construction. A distal portion of sheath 38 surrounding distal shaft section 24 is preferably formed from polytetrafluoroethylene (PTFE) to reduce friction as this portion of catheter 10 is introduced and withdrawn from the myocardium of the patient's heart. The insulation near tip 16 should also be resistant to high temperatures.

In an exemplary embodiment, the total length of the catheter is approximately 150 cm long. The distance from the extreme distal end of tip 16 to the leading or distal end of hood 18 is preferably approximately 7 mm, or the desired depth of the channels to be cut into the patient's myocardium. In this embodiment, the position of the hood relative to tip 16 is fixed by bond 40. The length of intermediate section 22 is preferably approximately 14 cm. Tip 16 is preferably formed from radiopaque metal having a diameter of approximately 1 mm. It should be understood that the dimensions given above are exemplary only and the variations in these dimensions may be made within the scope of the invention. Section 22 could also be of coil shaft construction as described below so long as an RF conductive connection is provided between sections 20 and 24.

FIG. 2 shows an alternate embodiment 110 of an RF TMR catheter in accordance with the present invention. RF TMR catheter 110 includes an elongate shaft 112. A manifold 114 is preferably disposed at the proximal end of shaft 112 and an RF cutting tip 116 is disposed at the distal end of shaft 112. A catheter advancement limiting hood 118 is disposed proximate and proximally of tip 116.

Shaft 112 preferably includes a proximal section 120 defined by a coil 142 having adjacent windings as shown covered by a sheath 144. Coil 142 preferably has adjacent windings for pushability and certain mechanical advantages described in more detail below, as well as increasing column strength prior to buckling. Coil 142 and sheath 144 can be formed from biocompatible materials known to those skilled in the art of catheter construction. For example, sheath 144 can be formed from a heat shrink polymer.

Shaft 112 also includes a distal section 124 bonded to the distal end of proximal shaft section 120 at 146. Shaft 124 preferably is formed from a tube such as a stainless steel hypotube.

A lead 126 is connected to a core wire 148 extending from manifold 114 through proximal shaft section 120. Core wire 148 has a distal end bonded at 150 to distal shaft section 124. Shaft section 124 in turn has a distal end bonded to tip 116. Each of these bonds should be able to conduct RF energy such that RF energy can be delivered to tip 116 through lead 126, core wire 148 and distal shaft section 124.

Core wire 148 may taper distally as shown to enhance flexibility of catheter 110 distally. For example, core wire 148 may taper from an outside diameter of 0.013 inches to 0.010 inches. Core wire 148 and distal shaft section 124 are preferably surrounded by an insulating sheath 138 to contain RF energy along the length of the catheter. Those materials discussed above with respect to sheath 38 are equally applicable to sheath 138 particularly with respect to the portion of the sheath covering distal shaft section 124 being preferably PTFE. Tip 116 can be formed in the size and from the materials described above with respect to tip 16, including a lumen 132 extending therethrough. Shaft 112 can be hydrophilically coated.

Proximal shaft section 120 defines a lumen 134 extending between manifold 114 and shaft section 124. The proximal end of lumen 134 is in fluid communication with port 136 of manifold 114. Distal shaft section 124 defines yet another lumen 152 in fluid communication with lumen 132 through tip 116, and lumen 134 through proximal shaft section 120 through side ports 154 through a proximal portion of distal shaft section 124. It should be noted in this regard that the distal end of lumen 134 is sealed around distal shaft section 124 by bond 146. With this arrangement of lumens, drugs and dyes can be infused and tissue and fluids aspirated as described above with respect to catheter 10. Proximal shaft 120 would be a hypotube shaft like shaft 20 above.

Figure 4:
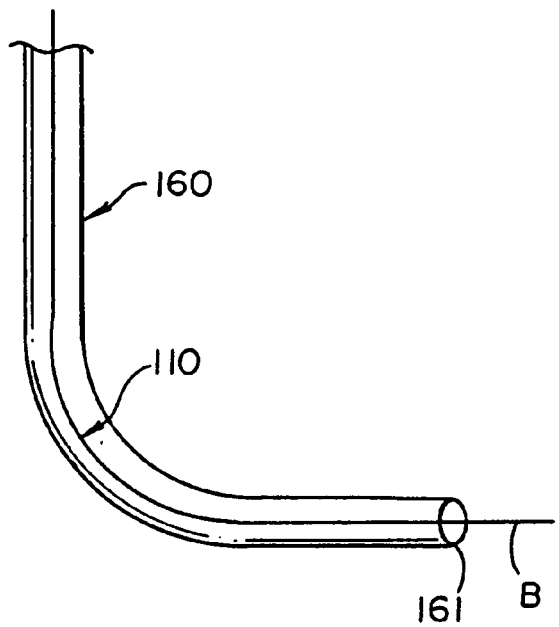
FIG. 4 is a schematic view of the coil shaft catheter of FIG. 2 advanced through a guide catheter.

FIGS. 3 and 4 schematically show an advantage of coil shaft construction such as that described above with respect to catheter 110. In FIG. 3, the guide catheter 160 is shown having a conventional bend proximate its distal end 161. The identical guide catheter 160 is shown in FIG. 4 as well. A catheter 162 having a polymer shaft has been advanced through catheter 160 beyond the bend and out the distal end 161. As the polymer from which catheter 162 is formed has a "memory" it retains a curve at A which reflects the curvature of catheter 160 through which catheter 162 has passed (here curve A is exaggerated). In FIG. 4, however, although catheter 110 is advanced in the same way as catheter 162 in FIG. 3, no bend is present along catheter 110 at B. At B catheter 110 is shown extending parallel to distal tip 161. It can be appreciated that as catheter 110 at B does not bend as catheter 162, catheter 110 can be precisely aimed in the same direction as distal tip 161. Catheter 162 does not have the same convenient relationship to the aiming of distal tip 161.

Figure 5:
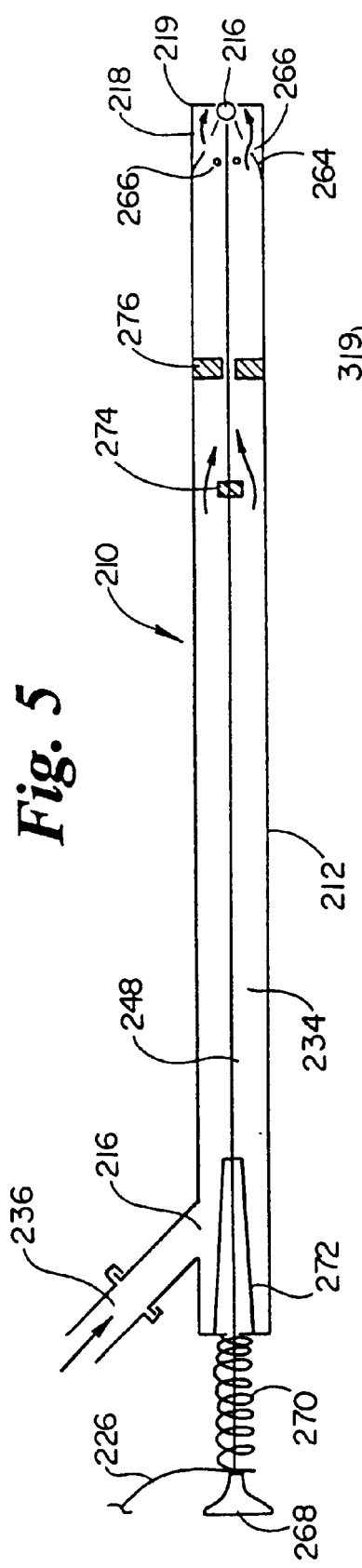
FIG. 5 is an alternate embodiment of an RF TMR catheter in accordance with the present invention.

FIG. 5 shows yet another embodiment of a TMR catheter 210 in accordance with the present invention. Catheter 210 includes a tubular shaft 212, which could be, for example, coiled shaft or combination of hypotube proximal and coil distal, having at its proximal end a manifold 214 and at its distal end, a hood 218 and cone shaped centering device 264. Shaft 212 defines a lumen 234 which at its proximal end is in fluid communication with a port 236 of manifold 216. The distal end of lumen 234 is interrupted by centering device 264, however, apertures 266 are provided to allow fluid flow through centering device 264. The distal end of shaft 212 which defines hood 218 is open and unobstructed for fluid flow into or out of shaft lumen 234.

A core wire 248 extends longitudinally through shaft 212. At the proximal end of core wire 248 is a push handle 268 biased proximally by a spring 270. The proximal end of shaft 212 is sealed about core wire 248 by wire seal 272. Wire seal 272 is preferably a close tolerance seal. At the distal of core wire 248 is a cutting tip 216. Cutting tip 216 is preferably radiopaque, metallic and spherical. RF energy is delivered to tip 216 by way of core wire 248 which at its proximal end is connected to an RF energy source by lead 226.

Stops 274 and 276 are connected to core wire 248 and shaft 212 respectively. As shown in FIG. 5, stops 274 and 276 are disposed within shaft 212. The longitudinal spacing of stops 274 and 276 is such that in a first position, ball 216 is within a hood 218 as shown. In a second position, stop 274 is advanced into contact with stop 276 and tip 216 extends beyond the distal end of shaft 212 a distance proportional to the depth of the channel to be formed in a patient's myocardium, for example 7 mm.

Saline or other fluids can be introduced through port tube 236 to lumen 234 for delivery to the distal end of shaft 212. If a vacuum is applied to port 236, fluids and tissue can be aspirated therethrough. Hood 218 includes a distal end 219 which preferably is atraumatic and includes a radiopaque agent.

The material of construction for making catheter 210 can be selected from those known to those skilled in the art of catheter construction. The materials should be biocompatible and have the mechanical properties desirable for which they are put to use.

Figure 6:
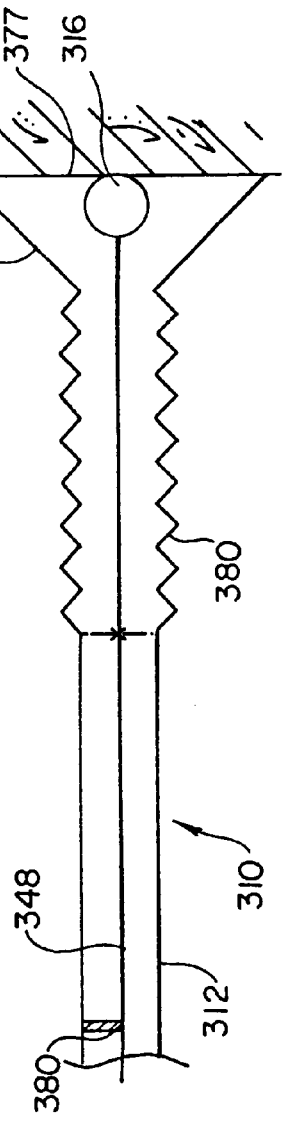
FIG. 6 is an alternate hood embodiment for the catheter of the present invention shown in a first position.
Figure 7:
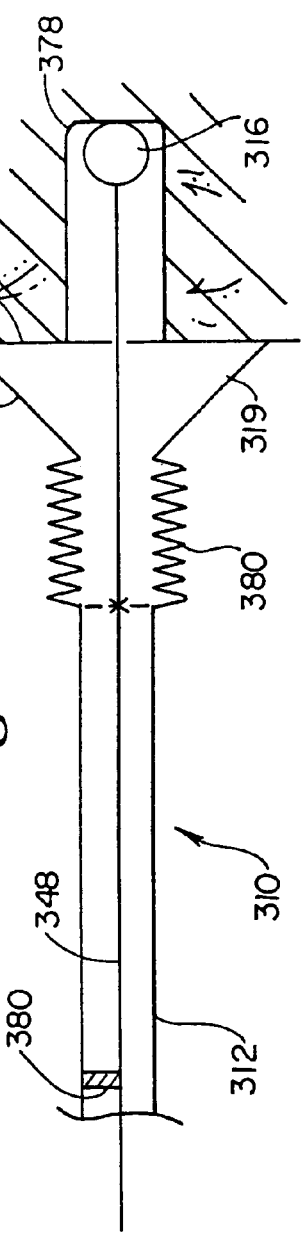
FIG. 7 is the hood of, FIG. 6 shown in a second position.

FIGS. 6 and 7 show schematically yet another embodiment of a TM catheter 310 in accordance with the present invention. Catheter 310 includes a shaft 312 and a core wire 348 which, unlike those elements in catheter 210, are held against relative longitudinal movement by a bond 380. A cutting tip 316 is provided at the distal end of core wire 348 which functions similarly to tip 216 of catheter 210 when connected to a source of RF energy.

Disposed at the distal end of catheter 310 is a hood 318 having a distal end 319. Distal end 319 is preferably atraumatic and may be radiopaque. In FIG. 6, hood 318 is shown surrounding tip 316 and distal end 319 is disposed against heart wall 377. An accordion-like structure 380 is disposed proximally of hood 318. As shown in FIG. 7, shaft 312 and core wire 348 have been advanced distally to collapse accordion-like structure 380 allowing tip 316 to form a channel 378 in a patient's myocardium. The accordion is spring-like, returning the hood to a first position covering the probe, after the probe is withdrawn.

Catheter 310 can be equipped with a proximal manifold (not shown) for infusion or aspiration of fluids. The materials used to make catheter 310 can be selected from those known to those skilled in the art of catheter construction.

In use, the various catheters disclosed herein can be delivered to a patient's myocardium through a guide catheter. The cutting tips of the catheters are advanced to the heart wall at the desired location. RF energy is then delivered to the cutting tips and the tips are advanced in the patient's myocardium. In the case of catheters 10 and 110, the depth of penetration will be limited by hoods 18 and 118 contacting the heart wall respectively. In the case of catheter 210, the depth of penetration will be limited by the engagement of stop block 274 on core wire 248 with stops 276 on shaft 212. In the case of catheter 310, the depth of penetration will be limited by the compliance of accordion-like structure 380. Mechanical stops such as those shown in FIG. 5 could also be used in combination with hood 318.

Incorporated herein by reference is U.S. Pat. No. 5,364, 393 to Auth et al., and U.S. patent application Ser. No. 08/812,425 entitled "TRANSMYOCARDIAL REVASCULARIZATION CATHETER AND METHOD" filed on date even herewith.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A TMR catheter, comprising:
   an elongate outer shaft having a proximal end and a distal end, and defining a lumen therethrough;
   an elongate inner shaft having a proximal end and a distal end, and extending through at least a portion of the shaft lumen to proximate the distal end of the outer shaft;
   a cutting tip disposed at the distal end of the inner shaft; and
   a hood disposed at the distal of the outer shaft, the hood being moveable, relative to the outer shaft and the inner shaft, between a first position proximate the tip and a second position proximal of the first position.

2. A catheter in accordance with claim 1, wherein the distal tip is disposed within the hood in the first position.

3. A catheter in accordance with claim 1, wherein the hood has an atraumatic distal end.

4. A catheter in accordance with claim 3, wherein the distal end of the hood is radiopaque.

5. A catheter in accordance with claim 1, wherein the hood includes a pleated, accordion-like, collapsible section which at least partially collapses as the hood moves from the first position to the second position.

* * * * *